United States Patent [19]

Täger et al.

[11] Patent Number: 5,330,536
[45] Date of Patent: Jul. 19, 1994

[54] FEMUR PORTION OF A HIP

[75] Inventors: Karl H. Täger, Gauting; Hans E. Harder, Probsteierhagen, both of Fed. Rep. of Germany

[73] Assignee: Howmedica GmbH, Schoenkirchen, Fed. Rep. of Germany

[21] Appl. No.: 629,053

[22] Filed: Dec. 14, 1990

Related U.S. Application Data

[63] Continuation-in-part of Ser. No. 244,447, Sep. 14, 1988, abandoned.

[30] Foreign Application Priority Data

Sep. 18, 1987 [DE] Fed. Rep. of Germany ....... 8712607

[51] Int. Cl.$^5$ ............................................. A61F 2/32
[52] U.S. Cl. ..................................................... 623/23
[58] Field of Search ..................... 623/16, 18, 20, 23; 606/64, 65

[56] References Cited

U.S. PATENT DOCUMENTS

| | | | |
|---|---|---|---|
| 3,466,670 | 9/1969 | Christiansen | 623/23 |
| 4,146,936 | 4/1979 | Aoyagi et al. | 623/23 X |
| 4,199,824 | 4/1980 | Niederer | 623/23 |
| 4,266,302 | 5/1981 | Tornier | 623/23 |
| 4,287,617 | 9/1981 | Tornier | 623/23 |
| 4,495,664 | 1/1985 | Blanquaert | 623/23 |
| 4,595,393 | 6/1986 | Anapliotis et al. | 623/22 |
| 4,743,263 | 5/1988 | Petrtyl et al. | 623/23 |
| 4,892,550 | 1/1990 | Huebsch | 623/22 |
| 4,895,572 | 1/1990 | Chernoff | 606/64 |
| 4,904,262 | 2/1990 | Bensmann | 623/18 |

FOREIGN PATENT DOCUMENTS

| | | | |
|---|---|---|---|
| 0065481 | 11/1982 | European Pat. Off. | 623/22 |
| 0243585 | 11/1987 | European Pat. Off. | 623/23 |
| 0329019 | 8/1989 | European Pat. Off. | 623/18 |
| 2851598 | 6/1980 | Fed. Rep. of Germany . | |
| 2933271 | 3/1981 | Fed. Rep. of Germany | 623/22 |
| 2933271 | 3/1981 | Fed. Rep. of Germany | 623/22 |
| 2090745 | 7/1982 | United Kingdom | 606/65 |

*Primary Examiner*—David Isabella
*Attorney, Agent, or Firm*—Peter C. Richardson; Lawrence C. Akers; Elizabeth O. Slade

[57] ABSTRACT

Femoral portion of a hip prosthesis comprising a shank, preferably a collar and a neck, with a ball-like head or a head-receiving portion being integrally formed to the neck, respectively, whereby the shank is formed as hollow body which comprises a plurality of openings interconnecting the lateral surfaces of the shank and the hollow space of the shank.

1 Claim, 5 Drawing Sheets

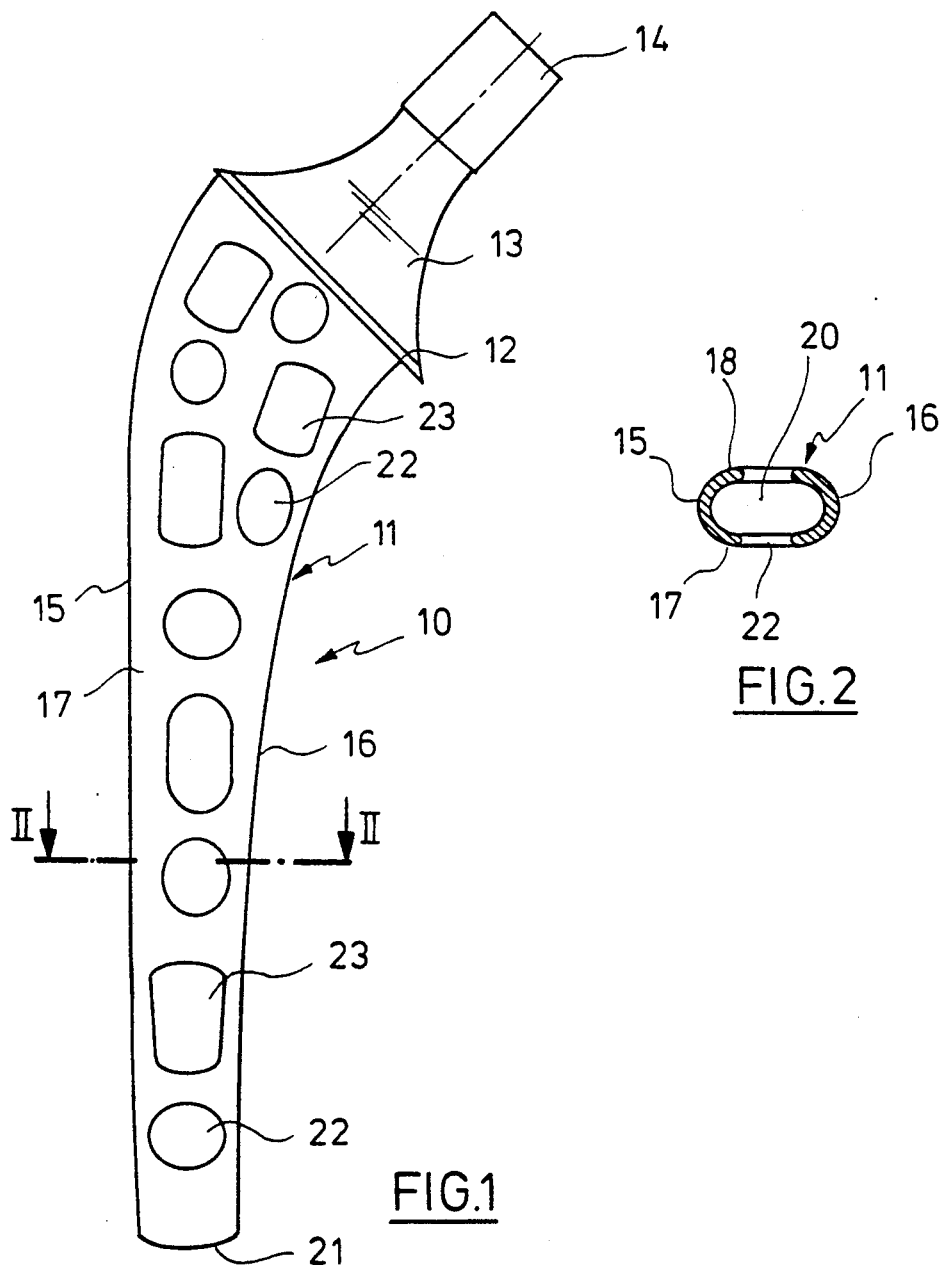

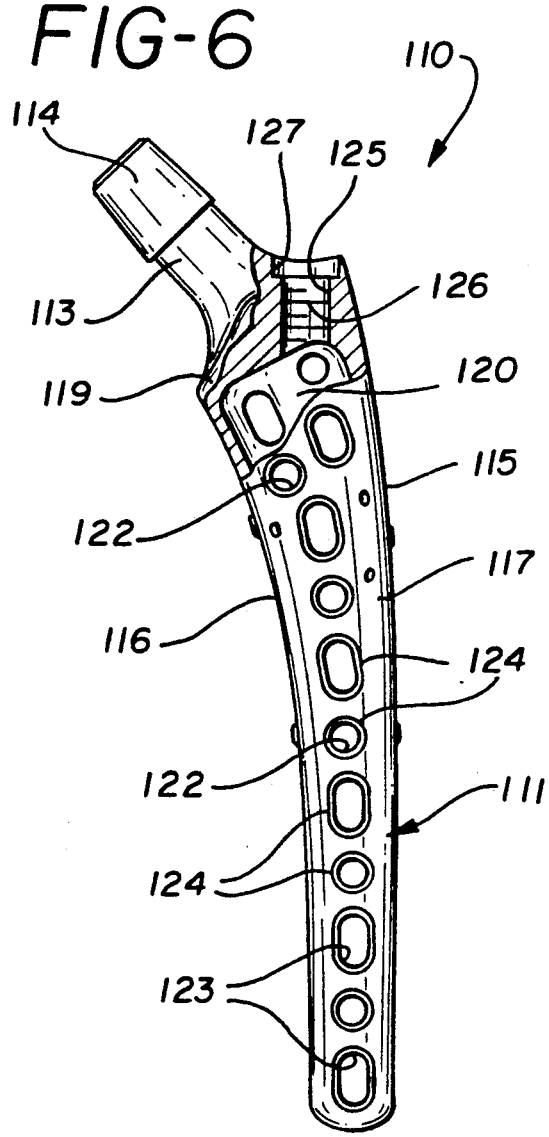
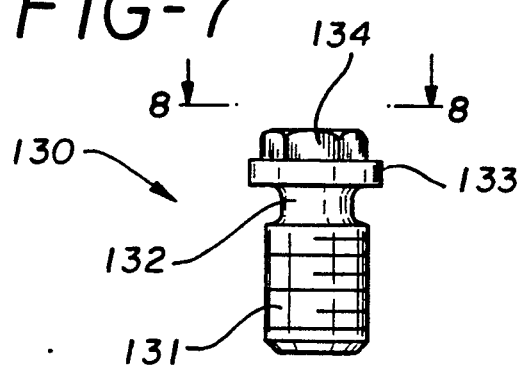
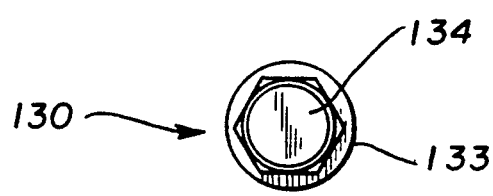
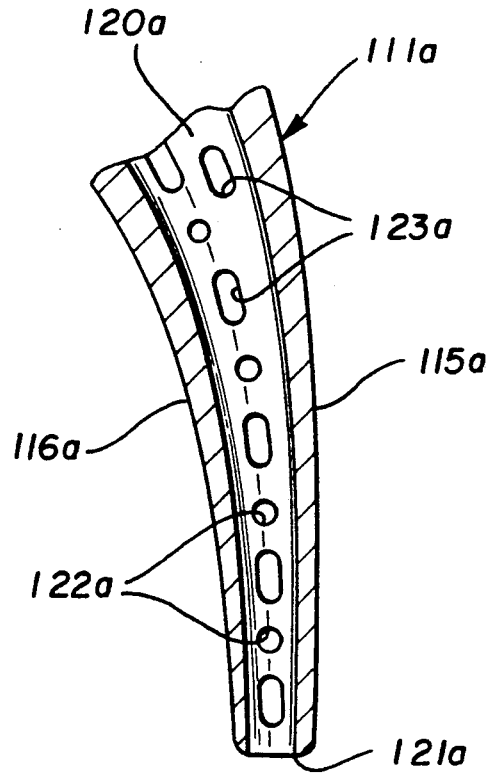

FEMUR PORTION OF A HIP

This is a continuation-in-part, of application Ser. No. 07/244,447, filed on Sep. 14, 1988 now abandoned.

The invention refers to a femoral portion of a hip joint prosthesis.

BACKGROUND OF THE INVENTION

For the use of known endoprostheses for hip joints there is a principal alternative to secure the femoral portion in the femoral canal either with or without bone cement. The use of bone cement enables an intimate and secure connection between the shank and the bone. However, the danger encounters that so-called micro motions lead to a loosening of the shank in the bone cement which may cause a malfunction of the endoprosthesis. A surgical reoperation then is necessary. However, it requires considerable efforts to remove femoral portions implanted with bone cement.

With cementless shanks it is attempted to achieve an effective power transfer from the shank to the bone. For this, it is prerequisite that the shank is held in the bone canal under considerable tension. The removal of such a shank is much more simply than a shank implanted with aid of bone cement. However, a cementless shaft effects a higher load of the bone so that distortions of the bone may occur during the implantation operation. In order to achieve an intimate contact between a cementlessly implanted shank and the bone, it is known to provide the shank with surface irregularities, indentations or the like or to give the surface a predetermined geometric structure. The bone tissue is to grow into the indentations or irregularities after implantation and to improve the fixation of the shank or the load transfer, respectively.

It is also known to improve the ingrowth of the prosthesis shank in that the spaces between the shank and the intermedullary canal are filling with spongy material. Normally, body-own spongy material is used which is removed for example by the surgeon from the hip bone.

From the German Gebrauchsmuster DE-Gm 87 12 607, a femoral portion has become known having a stem formed as hollow body including a plurality of openings connecting the hollow space within the stem with the outer surface thereof. The openings are preferably formed at the front and the dorsal side and can have various configurations. The hollow stem has the advantage that it can be filled with body-own autologeous or heterologeous spongy material enabling a genuine bony ingrowth of the prosthesis in the femur by a genuine bony connection so that a secure anchoring can be achieved without deterioration over a longer period. With these prostheses, the problem arises that the spongy material has to be inserted through the lateral openings which is somewhat difficult for the surgeon. In particular, it is difficult to charge the shaft such that the shaft accommodates a uniformly distributed and compressed mass.

The object of the invention is to provide a femoral portion of a hip joint prosthesis which can be implanted without bone cement, however, enables an intimate connection with or a genuine ingrowth of the adjacent bone portions, respectively.

The object of the invention is to design an effective configuration for the stem of a hip joint prosthesis by which the charging with spongy material is facilitated.

This object is attained by the device of the invention.

SUMMARY OF THE INVENTION

Conventional femoral portions of hip joint prostheses are solid and are normally formed by a casting process of metals or metal alloys compatible to a body. The shank of the femoral portion according to the invention is formed as hollow body and includes a plurality of openings which connect the hollow space of the shank with the outer surface of the prosthesis.

With the invention it has been recognized that a sufficient stability can be achieved if the prosthesis is made as a hollow profile. A hollow body has the advantage that it can be filled with spongy bone material. The surgeon during the operation can fill in body-own autologeous or heterologeous spongy material. Further, hydroxyl apatite can be used which is known in connection with artificial roots of teeth. The spongy material within the hollow body of the shank and in the opening enables an ingrowth of the prosthesis in the femur by a genuine bony connection so that a secure anchoring can be achieved unharmed over a longer period.

Since the prosthesis shank is mostly loaded on the lateral and the medial side (tension and pressure load), it is according to an embodiment of the invention advantageous if the openings are formed at the front and the rear side of the prosthesis shank.

According to a further embodiment of the invention, the distal end of the shank provides a free access to the hollow space of the shank. The passage within the interior of the prosthesis shank thus also opens to the distal end. This is advantageous for the introduction of spongy bone material, the improved ingrowth and for casting purposes.

The openings can have a different shape, preferably circular and/or elongated openings are used. If both kinds of openings are used, they preferably alternate.

The number of openings normally depends upon their distance from each other or their dimensions, respectively. Preferably the dimensions are such that the openings cover more than half of the distal area, preferably more than two thirds of the width of the shank. The distance of the openings is preferably smaller than the diameter of the circular openings. The total surface area of all openings thus is preferably at least as large as the unbroken remaining surface area. Preferably, the total surface of the openings is larger than the remainder. By this, the corresponding shank surfaces are screen-like and enable a connection of the hollow space of the shank with the environment through a relatively large cross-sectional surface area.

The edges of the openings are preferably rounded. Also the edges of the shank are rounded which, however, is known.

The femoral portion according to the invention consists of a body-compatible material. Preferably titanium or chromium nickel cobalt alloy is used. The shank can be cast or forged. The latter process is preferred.

A collar can be provided at the proximal end of the shank, however, the shank can be also missing a collar. Further, preferably a so-called retraction eye is provided which enables a simple removing of the shank upon a re-operation. According to a further embodiment of the invention, this eye can be formed to a vane or fin in the proximal portion of the shank, which feature gives the shank also a rotational stability, i.e. secures the shank against rotation.

The openings also permit in case of fractures to carry out an osteosynthesis by plates and/or screws.

If the openings are provided in opposite surfaces of the shank, they can be aligned along a direction perpendicular to the shank axis. However, it is preferred that the openings are offset to achieve an improved ingrowth of the bone.

With the prothesis according to the invention, the collarless end portion of the stem at the transition to the neck is solid. A bore is formed in the solid portion laterally of the neck, with the axis of the bore being aligned with that of the stem cavity. Spongy material can be inserted into the cavity through the bore, also after the stem has been inserted into the femur. The position or the arrangement of the bore, respectively, enables the spongy material to be compressed to a desired extent by a suitable tool. A certain compression of the material is desired to prevent it from dropping out from the openings before the stem is placed in the femur end to effect optimum growth conditions.

As already mentioned, the spongy material can be compressed by a suitable tool from above. An alternative embodiment of the invention includes a threaded bore for the accommodation of a threaded bolt. The threaded bolt serves as a plug which compresses the material below as it is threaded inwardly.

According to another embodiment of the invention, the upper end or proximal portion of the bore has a portion of larger diameter for the accommodation of a head of the bolt. The bolt head may cooperate with a shoulder within the bore and may provide an impact surface allowing the stem to be driven into the femur during operation. A separate impact surface has the advantage that the material of the stem is not damaged by the impact tool during operation which may affect the life time of the prosthesis.

According to a further embodiment of the invention, the bolt head includes a cylindrical or flange portion and tool engaging surfaces above the cylindrical portion, preferably a hexagon, with the cylindrical portion being fittingly accommodated by the enlarged bore portion, and the outer dimensions of the tool-engaging surfaces are smaller than the diameter of the cylindrical portion. Particularly, if the tool-engaging surfaces project beyond the bore, the threaded bolt can be rotated out of the implanted stem in order to achieve an access to the interior of the stem cavity. Besides, a retracting element may be threaded into the bore if the stem must be removed for reoperation purposes.

In the femoral portion according to the invention, the elongated openings may have an oval shape. All openings include a chamfer of the outer edge such that a constricting entrance area is formed. According to an embodiment of the invention, the diameter of all openings or the length of all oval openings, respectively, are equal, with the width of the oval openings corresponding to the diameter of the circular openings. The conical entrance portion has the advantage that the spongy material can be more easily inserted from lateral because it forms a kind of funnel, and the chamfer reduces stress peaks which may occur upon load.

In the proximal area, two generally vertical rows of openings are provided, both rows having a circular and an oval opening with an oval opening as the upper one of the medial row, and a circular opening as the upper one of the lateral row. With this design, a favourable distribution of the different types of openings is achieved resulting in a good ingrowth of bony substance and a sufficient stability of the stem in the proximal area.

The invention is hereinafter explained with drawings.

BRIEF DESCRIPTION OF THE DRAWINGS

FIG. 1 is a diagrammetric lateral view of a femoral portion of the endoprosthesis according to the invention.

FIG. 2 is a cross section through FIG. 1 along line II—II.

FIG. 6 is a similar side view as FIG. 3, however, partially in cross section.

FIG. 7 shows a threaded plug for the prosthesis of FIG. 3 or 6, respectively in an enlarged scale.

FIG. 8 is an end view of the plug of FIG. 7 in the direction of arrow 8—8.

FIG. 9 is a longitudinal section through a portion of a stem for a prosthesis according to the invention.

Figure 3:
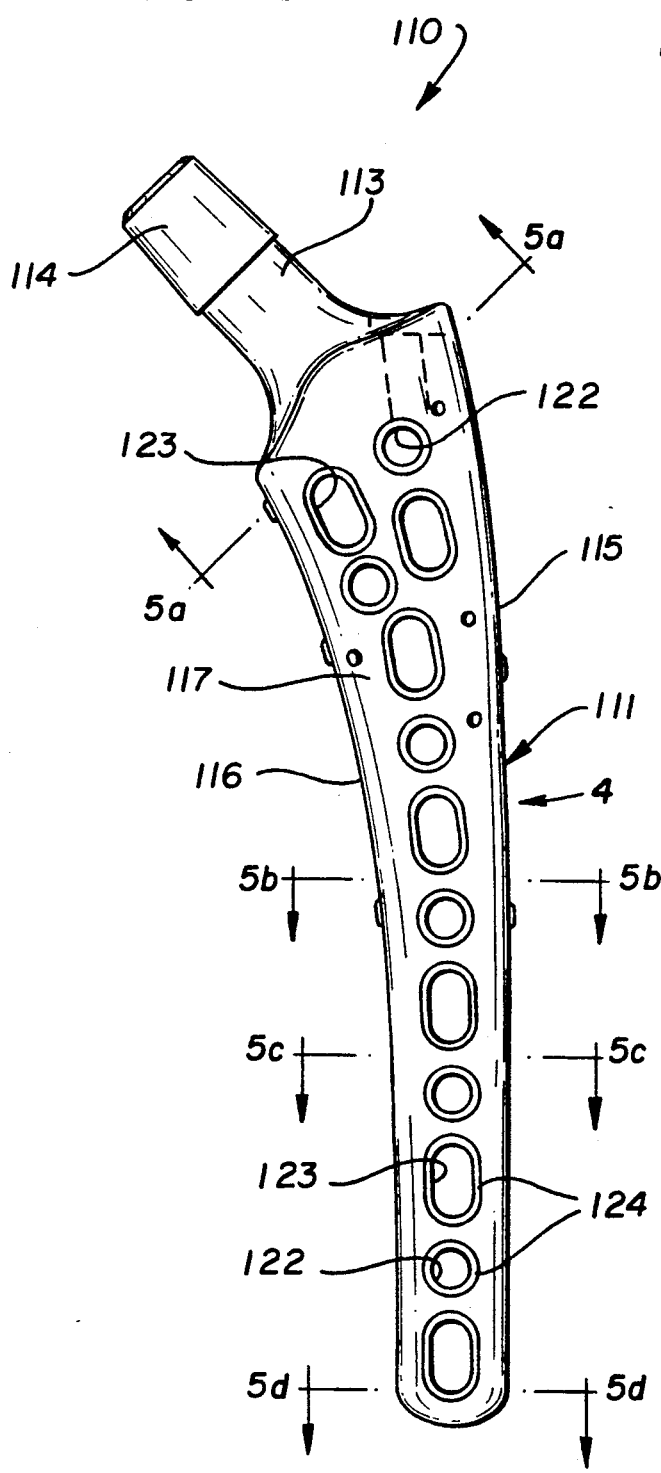
FIG. 3 is a side view of a prosthesis according to the invention.

Before going into detail, it is to be noted that each of the described features per se or in connection with features of the claims can be significant to the invention.

DETAILED DESCRIPTION OF THE DRAWINGS

FIG. 1 shows a femoral portion 10. It consists of a relatively elongated slim shank 11, a collar 12 and a conical neck 13, the neck having a cone 14 at its end for receiving a joint ball which is provided with a mating inner cone. The angle between the shank and the neck axis is about 135°.

The shank 11 has a lateral side 15 and a medial side 16. It is assumed that the visible side of the shank is the front one. The dorsal side is designated with 18 (FIG. 2). It can be seen in FIG. 2 that the front and the dorsal side 17, 18, respectively are approximately parallel and that the medial side 16 and the lateral side 15 are arcuately curved. It is of particular significance that the shank 11 includes a hollow space 20 which extends like a canal through the length of the complete shank. The hollow space 20 is opened to the distal end 21 of shank 11. The front side 17 of shank 11 is provided with a series of openings which extend from the distal to the proximal end of shank 11 with the circular openings 22 alternating with elongated openings 23. The openings 22 have a diameter which is larger than the half width of the shank or the front side, respectively. The width of the openings 23 corresponds to the diameter of the openings 22. The length of the opening 23 is approximately as large as double the diameter of the openings 22. A second row of openings 22, 23, respectively, is provided in the proximal area. It can be seen that a large part of a front side 17 is provided with openings or apertures. It can be larger than the share of the non-apertured surface. The opposite rear side 18 of shank 11 is in a similar manner provided with openings as shown in FIG. 1 which preferably are offset with respect to the openings of side 17.

The shown shank 11 is made hollow since it is adapted to be filled with body-own or heterologous spongy material or a similar substance promoting the ingrowth of the shank in the bone. The holes or openings 22, 23 enable that the spongy material in shank 11 grows jointly with the spongy material in the bone canal or the remaining bony substance, respectively.

In the shown embodiment the shank 11 is throughout hollow. It is understood that under certain circumstances it can be sufficient to make shank 11 partially hollow in order to obtain the desired effects.

Figure 4:
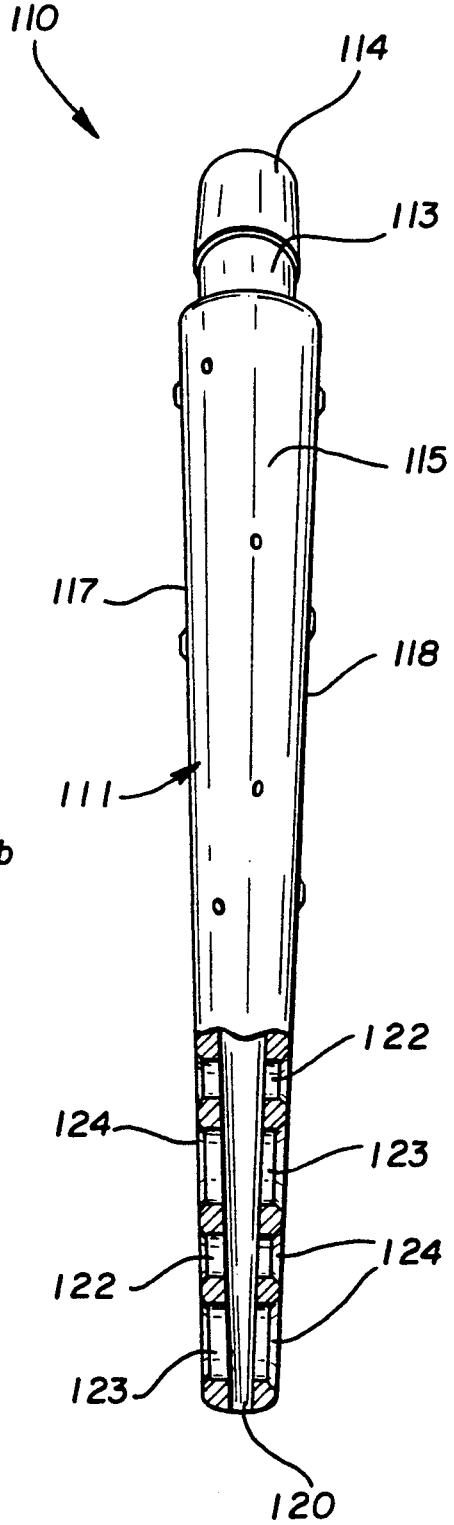
FIG. 4 is another side view of the prosthesis of FIG. 3 if looking in the direction of arrow 4.
Figure 5A:
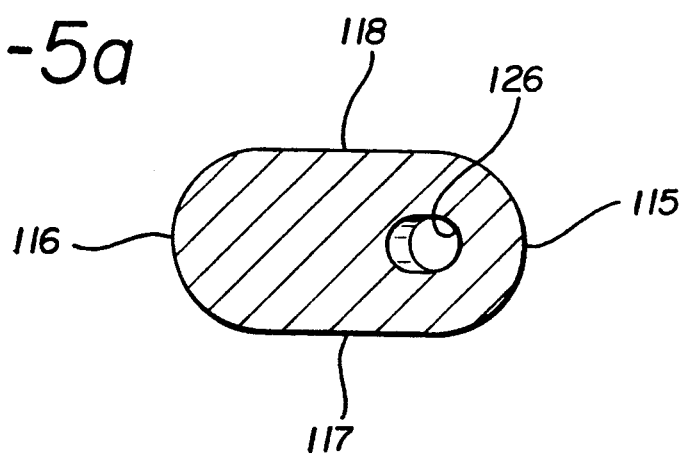
FIG. 5 shows individual cross sections through the prosthesis of FIG. 3.
Figure 5B:
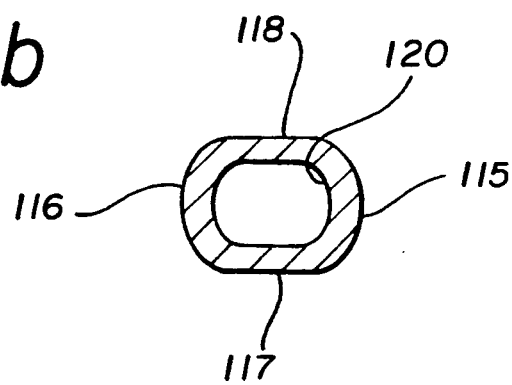
Figure 5C:
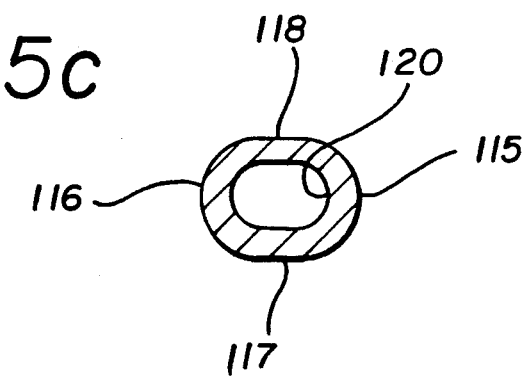
Figure 5D:
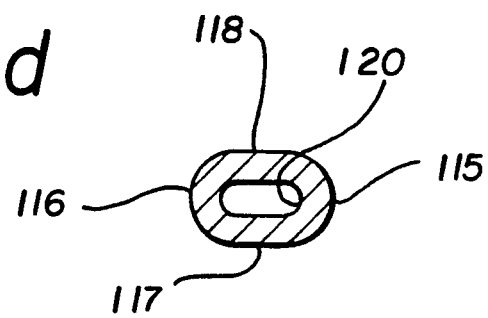
Figure 10:
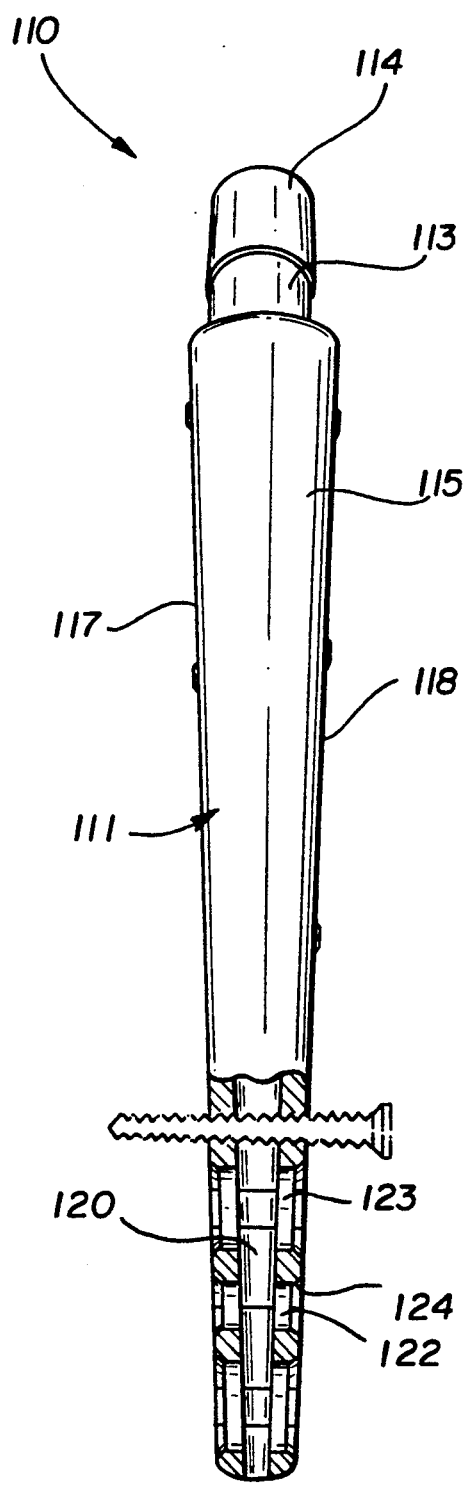
FIG. 10 is the same as FIG. 4 but shows additionally a bone screw indicated by phantom lines, showing how the circular bores may accommodate bone screws.
Figure 11:
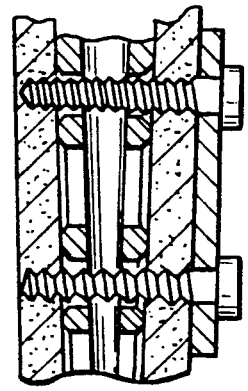
In FIG. 11, two bone screws are shown inserted through a prosthesis of the invention and through a plate.

In FIGS. 3 and 4 a femoral portion 110 is shown. It consists of a relatively slim generally hollow tubular stem 111 which merges into a conically tapering neck 113 at the proximal end without a collar, the neck 113 having a cone 114 to receive a joint ball (not shown) which has a mating inner conical bore. The angle between the stem axis and the neck axis is about 135°. A collarless stem is preferred, however, a collar can be provided if required for other reasons.

The stem 111 has a lateral side 115 and a medial side 116. The visible front or anterior side is designated by 117 while the dorsal or posterior side is designated by 118 (see FIGS. 4 and 5). As can be seen in FIG. 5, the front side 117 and the dorsal side 118 are approximately parallel and the medial side 116 and the lateral side 115 are arcuately curved.

The stem 111 has an interior hollow space 120 which extends through the length of the complete stem. The hollow space 120 is opened to the distal end 121 of shank 111. The proximal end of the hollow space terminates at a solid upper end 119 of shank 111, the proximal surface of the hollow space 120 extending approximately perpendicularly to the axis of neck 113. The thickness of portion 119 depends upon the desired strength by which the neck 113 is to be supported by shank 111.

The front side 117 and the dorsal side 118 of the shank 111 are provided with circular openings 122 and oval openings 123. A first vertical row or column of openings 122, 123 which alternate, extends along the center line of shank 111 or parallel therewith, respectively, of the posterior end of stem. A second vertical row consisting of a circular opening 122 and an oval opening 123 extends substantially parallel to the first row, the first row having an oval opening at the proximal end and a circular opening therebelow while the sequence is reversed in the parallel row. As can be seen further, the second row is substantially aligned with the openings 122, 123 which extend below, with the line connecting the centers of the openings with the lateral portion of the shoulder between shank 111 and neck 113 and the distal end 121. This line is substantially parallel to the axis of the femur. The circular openings 122 have the same diameter. The width of the oval openings 123 corresponds to the diameter of the circular openings 122. The shape of the openings 122, 123 and the sequence thereof allow a maximum ingrowth surface area without the strength of the stem being unduly reduced. The length of the oval openings corresponds to the double of the diameter of the circular openings. The longitudinal axis of the oval openings 123 in the center and the distal area is substantially parallel to the longitudinal axis of shank 111. The edges of the openings 122, 123 have a chamfer 124 by which a funnel-like entrance portion to the hollow space 120 is formed. The chamfer, further, reduces stress concentrations at the edges of the openings. The wall thickness of the shank in the range of hollow space 120 is substantially constant so that the hollow space 120 continuously narrows toward the distal end. The conical design of space 120 facilitates the compression of spongy material from above.

A bore 125 is formed in the solid portion 129 on the lateral side of neck 113, the axis of the bore being substantially aligned with the longitudinal axis of shank 111 or the hollow space 120, respectively. The bore 125 has a threaded portion 126 extending down to hollow space 120. At the upper end, the bore portion 126 merges into a portion 127 of larger diameter. The bore 125 accommodates a threaded plug 130 which is shown in FIGS. 7 and 8 in more detail. The plug 130 includes a threaded shank 131 joined by a neck portion 132 of smaller diameter, a cylindrical portion or flange 123 joining the neck portion. A hexagonal head 134 is provided above flange 133, the maximum diameter of the hexagonal head being smaller than the diameter of flange 133. The threaded plug 130 is threaded into the threaded bore 125 after the hollow space 120 has been filled up with a spongy material. The filling of the hollow space takes also place through openings 122 and 123. It is to be mentioned that the openings 122, 123 are registering on opposing sides. By means of the threaded plug 130, the material within bore 125 and therebelow is compressed. The amount of compression depends on the amount of material inserted. If necessary, the plug 130 can be removed to insert additional material and to repeat the compression. For compression purposes, the threaded plug 131 extends beyond the lower end of bore portion 126 when flange 133 is matingly accommodated by the enlarged bore portion 127. The hexagonal head 134 serves for the rotation of plug 130. It extends beyond the upper surface of the proximal end of shank 111 so that it can be engaged by a wrench both during threading in and upon removal of plug 130. The head 134 further serves as impact surface to drive the prosthesis 110 into the femur. In case the femur is to be removed, the plug 130 is removed and another element is threaded in which, for example, can have a retracting portion, for example an eye or the like to drive the prosthesis 110 out of the femur.

It is preferred that the prosthesis shown is casted e.g. of titanium or body-compatible chromium cobalt nickel alloy (Vitallium). However, it can also be made by other known techniques already known.

In the embodiment of FIG. 9 it can be seen that the partially illustrated stem 111a has a wall thickness which continuously reduces downwardly in the lateral/medial plane. For example, in the upper part, the thickness is 4 mm while in the lower part, the thickness is 3 mm. In the anterior/posterior plane, however, the thickness is constant throughout the length of stem 111a.

We claim:
1. The femoral portion of a hip joint prosthesis comprising:
 (a) a monolithic shank having a length L, a hollow space therewithin having an axis, a distal end, outer surfaces, and a posterior side, a medial side, an anterior side, and a lateral side, wherein the shank is formed as circumferentially closed hollow body throughout at least a major portion of said length L and comprises a plurality of openings located on only each of said posterior side and said anterior side and interconnecting said outer surfaces of said shank and said hollow space of the shank wherein said distal end of the shank is open and provides a free access to said hollow space of said shank, (b) a neck and (c) a solid collarless end portion of said shank adjacent to said neck with a threaded bore having an axis formed in said solid end portion lateral of said neck, said axis of said bore being substantially aligned with said axis of said hollow space, wherein in the lateral—medial plane the wall thickness of said shank continuously reduces downwardly while in the anterior—posterior plane the thickness is constant throughout the length of said shank.

* * * * *